(12) United States Patent
Granegger et al.

(10) Patent No.: US 12,161,856 B2
(45) Date of Patent: *Dec. 10, 2024

(54) CONTROL DEVICE AND METHOD FOR A HEART PUMP

(71) Applicant: Berlin Heart GmbH, Berlin (DE)

(72) Inventors: Marcus Granegger, Perchtoldsorf (AT); Constantin Wiesener, Potsdam (DE); Dominik Karch, Berlin (DE)

(73) Assignee: Berlin Heart GmbH, Berlin (DE)

( * ) Notice: Subject to any disclaimer, the term of this patent is extended or adjusted under 35 U.S.C. 154(b) by 1 day.

This patent is subject to a terminal disclaimer.

(21) Appl. No.: 18/145,426

(22) Filed: Dec. 22, 2022

(65) Prior Publication Data
US 2023/0128050 A1 Apr. 27, 2023

Related U.S. Application Data

(63) Continuation of application No. 15/755,006, filed as application No. PCT/EP2016/068991 on Aug. 9, 2016, now Pat. No. 11,590,337.

(30) Foreign Application Priority Data

Aug. 24, 2015 (EP) ..................................... 15182115

(51) Int. Cl.
*A61M 60/148* (2021.01)
*A61M 60/165* (2021.01)
(Continued)

(52) U.S. Cl.
CPC ........ *A61M 60/148* (2021.01); *A61M 60/165* (2021.01); *A61M 60/531* (2021.01);
(Continued)

(58) Field of Classification Search
CPC ................ A61M 1/1086; A61M 1/122; A61M 2205/3334; A61M 2205/3344;
(Continued)

(56) References Cited

U.S. PATENT DOCUMENTS 6,572,530 B1 6/2003 Araki et al.
6,623,420 B2 9/2003 Reich et al.
(Continued)

FOREIGN PATENT DOCUMENTS

CN 101983732 A 3/2011
CN 102365104 A 2/2012
(Continued)

OTHER PUBLICATIONS

First Office Action with English translation, issued in Chinese Patent Application No. 201680055521.4, dated May 8, 2020, pp. 1-20, China National Intellectual Property Administration, Beijing, China.
(Continued)

*Primary Examiner* — Jonathan T Kuo
*Assistant Examiner* — Vynn V Huh
(74) *Attorney, Agent, or Firm* — Crowell & Moring LLP

(57) ABSTRACT

A control device for a heart pump, comprising a device for establishing the end-diastolic filling pressure in a ventricle and a device for associating a delivery rate of the pump, in particular a pump speed or an electric pump capacity, with the established end-diastolic filling pressure. By taking into account the end-diastolic filling pressure, a robust operating option of the heart pump, similar to the physio-logical control, is created.

10 Claims, 2 Drawing Sheets

(51) Int. Cl.
  *A61M 60/531* (2021.01)
  *A61M 60/554* (2021.01)
(52) U.S. Cl.
  CPC ... *A61M 60/554* (2021.01); *A61M 2205/3334* (2013.01); *A61M 2205/3344* (2013.01); *A61M 2205/3358* (2013.01); *A61M 2205/3365* (2013.01); *A61M 2205/52* (2013.01); *A61M 2210/125* (2013.01)
(58) Field of Classification Search
  CPC .. A61M 2205/3358; A61M 2205/3365; A61M 2205/52; A61M 2210/125
  USPC ...................................... 600/16–18, 508–528
  See application file for complete search history.

(56) References Cited

U.S. PATENT DOCUMENTS

| | | | | |
|---|---|---|---|---|
| 2003/0045772 | A1* | 3/2003 | Reich | A61M 60/216 600/18 |
| 2007/0185369 | A1 | 8/2007 | Mirhoseini et al. | |
| 2008/0097226 | A1* | 4/2008 | McConnell | A61B 5/0215 600/16 |
| 2010/0192686 | A1* | 8/2010 | Kamen | A61M 1/3672 715/764 |
| 2010/0222633 | A1 | 9/2010 | Poirier | |
| 2015/0246166 | A1* | 9/2015 | Greatrex | A61M 60/216 600/17 |
| 2015/0306290 | A1* | 10/2015 | Rosenberg | A61B 5/0215 600/16 |

FOREIGN PATENT DOCUMENTS

| | | |
|---|---|---|
| WO | WO 03/015609 A2 | 2/2003 |
| WO | WO 2015/040221 A2 | 3/2015 |

OTHER PUBLICATIONS

International Search Report with English translation, dated Nov. 2, 2016, pp. 1-12, Issued in International Application No. PCT/EP2016/068991, European Patent Office, Rijswik, Netherlands.

* cited by examiner

CONTROL DEVICE AND METHOD FOR A HEART PUMP

RELATED APPLICATION

This application is a Continuation of U.S. application Ser. No. 15/755,006, filed Feb. 23, 2018, now U.S. Pat. No. 11,590,337, which claims priority to International Patent Application No. PCT/EP2016/068991 filed Aug. 9, 2016, which further claims priority under 35 USC § 119 to European patent application EP 15182115.4 filed on Aug. 24, 2015, all of which are hereby entirely incorporated by reference.

TECHNICAL FIELD

The embodiments relate to electrical engineering and can be used particularly advantageously in the field of medical technology. Specifically, the embodiments relate to a control device for a heart pump and to the detection of measurement variables intended to form the basis of the control.

BACKGROUND

For some years, heart pumps for delivering blood and for replacing or assisting a patient's heart have been known. Pumps of this kind can be embodied in various forms and can be operated in different ways. They can essentially replace the patient's heart and take on the function thereof fully, or can also be used merely to support a heart that is not capable of performing its full function.

DETAILED DESCRIPTION

Figure 1:
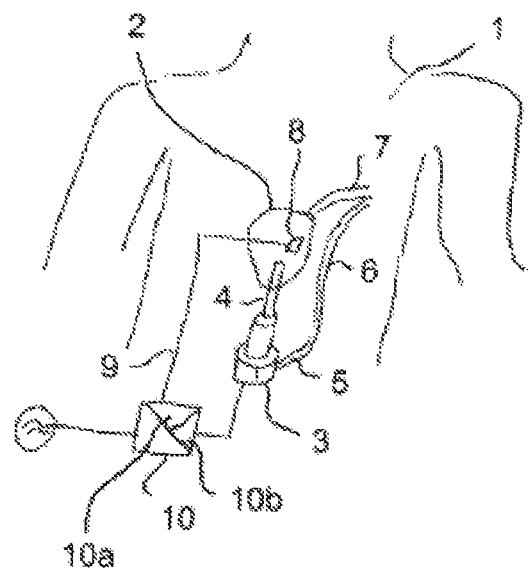
FIG. 1 shows a heart pump device comprising a control device.

Hereinafter, the application of a control system for a rotary pump will be considered as a particular example of the innovation, since pumps of this type can be controlled particularly easily in respect of the delivery capacity. However, this is not intended to rule out the application with other pump types that can be controlled in respect of their delivery capacity.

Rotary blood pumps are often operated at a constant speed in order to continuously relieve the load on the patient's heart. However, particularly when the patient performs physical activity or is physically burdened, this often leads to a reduced blood supply in the patient's body and/or to an overloading of the heart. The physical performance of the patient is therefore adversely affected.

Various control possibilities for heart pumps of this kind have been discussed in the literature, wherein detected operating parameters of the pump usually form the basis of a control operation. These possibilities have not yet been implemented in practice.

U.S. Pat. No. 6,623,420 discloses a control device for a blood pump comprising a pressure sensor in the ventricle. There, the minimum left-ventricular filling pressure is measured, and the control system keeps this filling pressure within a certain range. Here, there is in particular the problem that the absolute control range for the minimum ventricular pressure is small, since it is usually located in the flat region of the end-diastolic pressure/volume curve. A small change to the minimum ventricular pressure, in order to keep this constant, would entail a large change to the pump speed. This also means that a small error in the pressure measurement has a great effect on the change to the pump speed. Since pressure sensors are usually affected by drift, this drift alone of the sensor can lead to unsuitable control ranges of the speed.

In addition, there is the disadvantage that, in accordance with the prior art in the aforementioned US document, the minimum ventricular pressure is controlled to a target value. This does not correspond to the physiological principle of the Frank-Starling effect. This mechanism ensures an increase of the cardiac output on account of an increase of the preload. However, the preload is not controlled to a value by the heart, and instead is also significantly increased for example in the event of physical activity and high cardiac output. This increase of the left-ventricular preload also limits the cardiac output due to an increase of the right-ventricular afterload. This mechanism therefore balances the cardiac output of the right and left heart ventricles.

Against the background of the prior art, the object of the present innovation is to create a control system of the type mentioned at the outset for a heart pump, which control system responds as insensitively as possible to a drift of used pressure sensors and comprises as many elements as possible of a physiological control system.

An additional subject of this protective right is a heart pump or a heart pump system (i.e. heart pump plus peripheral equipment, such as power supply, etc.), which can contain all the features of the claims and the following description and drawings.

The innovation can be in the form of a control device for a heart pump, comprising a device for establishing the end-diastolic filling pressure in a ventricle and a device for associating a value of an operating parameter, in particular the delivery rate of the pump, more particularly a pump speed or an electric pump capacity, with the established end-diastolic filling pressure.

Part of the control device is therefore a device for establishing the end-diastolic filling pressure in a ventricle, which device for this purpose usually has a pressure sensor which not only can measure individual pressure values statically, but also makes it possible to establish a pressure profile in a ventricle. The usual pressure profile of the heart during the heart rate period is known. It is determined from the profile of the end-diastolic filling pressure in a ventricle. This is the pressure that prevails in a ventricle after the diastolic phase, prior to the contraction of said ventricle. The end-diastolic pressure has a greater variation range (approximately 0 to 30 mmHg) than the minimum ventricular pressure and is therefore less sensitive to small measurement errors or sensor drift.

On the basis of the pressure value reached when the end-diastolic filling pressure is reached, the control device determines parameters for the operation of the pump, in particular a delivery capacity or a pump speed that is to be achieved.

In order to realise the innovation, it is provided in particular that the control device is connected to an absolute pressure sensor arranged in the ventricle or to another pressure-measuring device. Here, it can additionally be provided that a device for correcting the measured absolute pressure under consideration of a determined atmospheric pressure is provided. By means of an additional correction device, for example with the aid of an additional pressure sensor, which is arranged outside the heart, pressure fluctuations outside the patient's body which would affect the measurement of the filling pressure can be eliminated.

The control device according to the innovation is characterised in that the target pressure is dependent in a variable manner in particular on the speed/delivery rate of the pump, the delivery rate of the heart, or a linking of both variables. Here, it is particularly important that the delivery rate or capacity of the pump is not focused on reaching a certain value of the end-diastolic filling pressure, and therefore a certain target value for the end-diastolic filling pressure can be set depending on the current and individual physiological conditions. This makes possible the integration of aspects of a physiological control system in the control system according to the innovation.

For example, it can be provided that the control device comprises a proportional controller. Thus, there can be deliberately no P/I controller (proportional/integral control) provided, which would initiate correction measures that would be dependent on the distance of the established end-diastolic filling pressure from a target value, such that certain fixed filling pressure values would be set after this procedure. The physiological control system in a healthy circulation system functions differently, such that different values for the end-diastolic filling pressure are reached depending on the load.

In principle, however, the use of a P/I controller within the scope of the innovation is not ruled out.

The present innovation in principle also allows control of the pump in a manner focused on reaching a certain target pressure value for the end-diastolic pressure of a ventricle.

Specifically, the control device can be designed in such a way that the control device comprises a memory device in which various ranges of the established end-diastolic filling pressure are each associated with a certain controller gain.

It can also be provided that the control device comprises a memory device in which various values of the established end-diastolic filling pressure are in each case associated with a value characterising the delivery rate of the pump, in particular a speed or an electric capacity of the pump or a value of another operating parameter of the pump.

Here, in accordance with an embodiment of the innovation, it can additionally be provided that a non-linear relationship exists in the memory device between the pressure values and controller gains and/or speeds and/or delivery rates of the pump.

In the simplest case the innovation can be implemented by a computer program product comprising a program that calculates and associates a speed/delivery rate of a pump with an established end-diastolic filling pressure in a ventricle and controls the pump to this delivery rate. Of course, the computer program product can also be designed so that it implements the methods described hereinafter for controlling a heart pump.

The innovation also relates to a control device of the above-mentioned type and a computer program product and to a method for controlling a heart pump under consideration of measured values of the blood pressure in a ventricle, wherein the control is based on the end-diastolic filling pressure in the heart chamber, and in particular the pressure in the heart chamber is measured by means of an absolute pressure sensor.

Here, a particular embodiment of the method provides that the end-diastolic filling pressure is variable in the form of a target variable of the control and in particular is dependent on the delivery rate of the heart, or the speed/delivery rate of the pump, or a linking of both values. To this end, it can be provided in particular that the control system establishes the target pressure under consideration of the delivery rate of the heart or the pump, or the speed of the pump, or a linking of these values.

To this end, one implementation provides that the control is a proportional control. In particular, the control can be embodied without an integral
controller.

In a further implementation of the method it can also be provided that the control system, by means of a memory device, in each case associates a value characterising the delivery rate of the pump, in particular a pump speed or a pump capacity, with a measured or established end-diastolic pressure value.

In addition, it can also be provided that the control device comprises a memory device, in which various ranges of the established end-diastolic filling pressure are each associated with a controller gain.

A further implementation of the innovation can provide that a plurality of pressure values are each associated with delivery rates of the pump or other operating parameter values of the pump in accordance with a relationship which in particular is a non-linear relationship.

Figure 2:
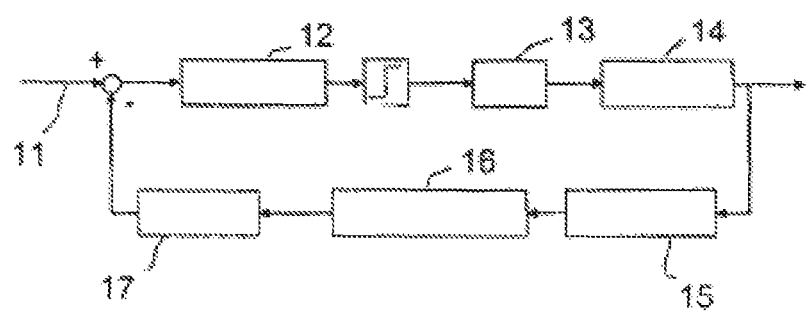
FIG. 2 shows a flow diagram of the control concept according to the innovation.
Figure 3:
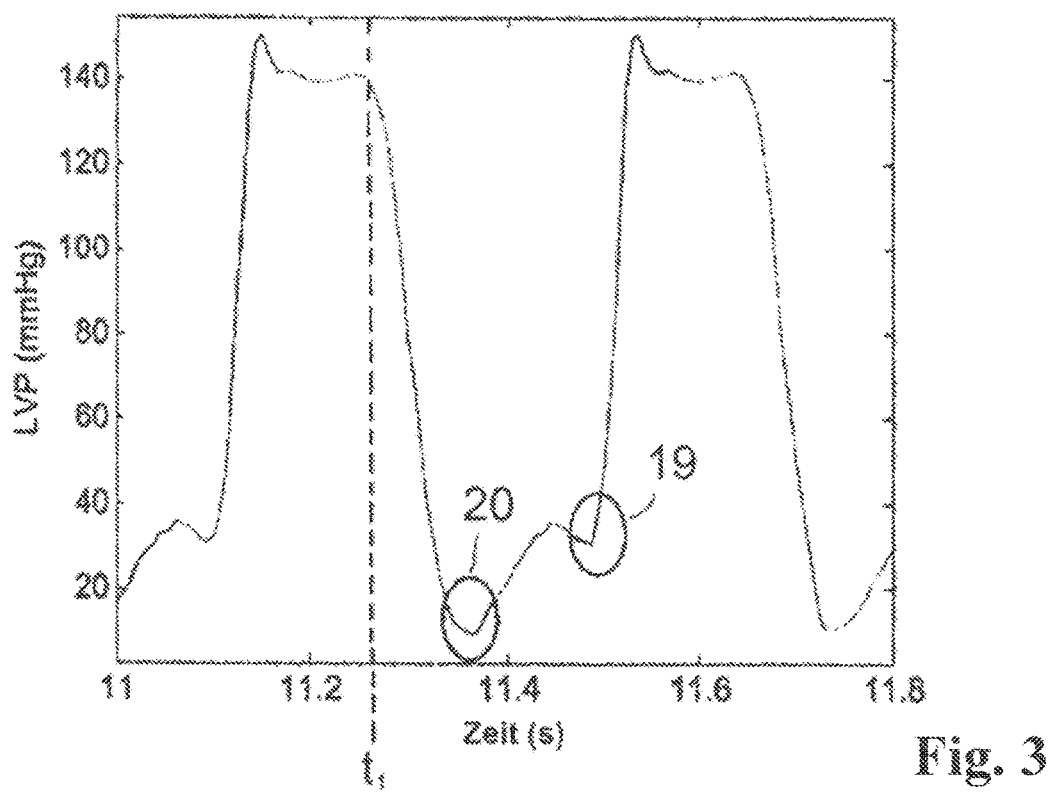
FIG. 3 shows a graph of the pressure profile during a cardiac cycle.
Figure 4:
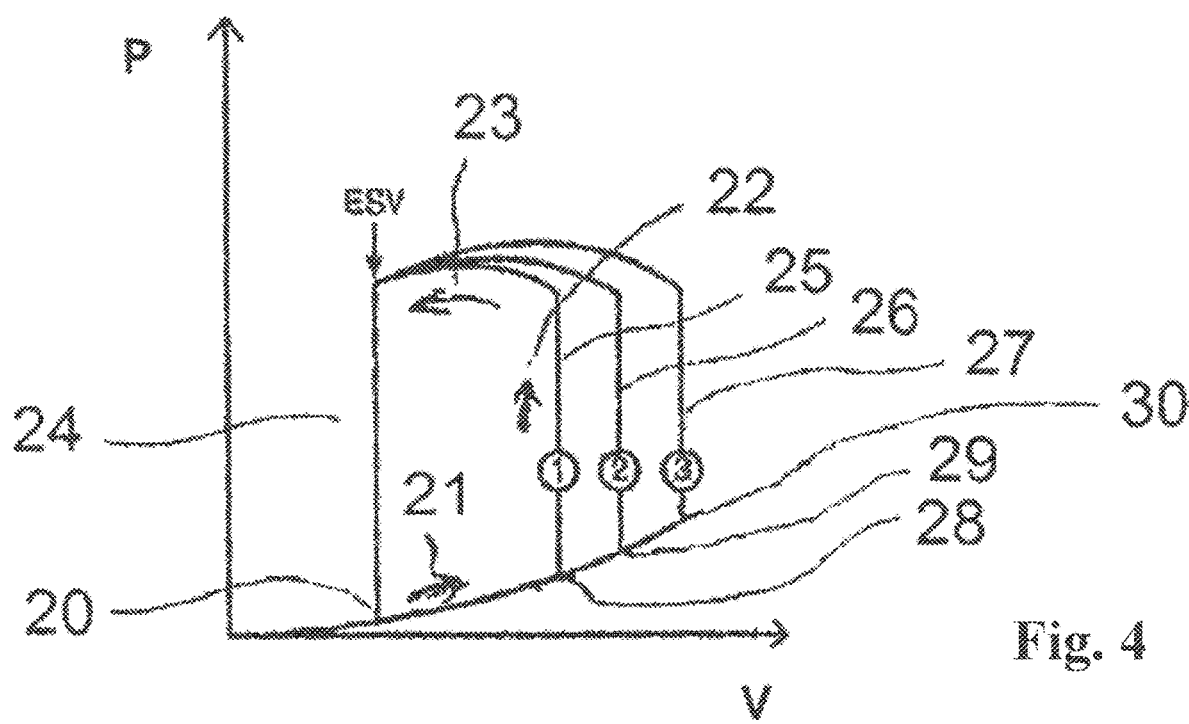
FIG. 4 shows a presentation of the pressure and the ventricular volume during the cardiac cycle in three standard cases with different end-diastolic filling pressure.

Hereinafter, exemplary embodiments of the innovation will be shown on the basis of figures of a drawing and will be explained further below. In the drawing FIG. 1 schematically shows a heart pump device comprising a control device, FIG. 2 schematically shows a flow diagram of the control concept according to the innovation, FIG. 3 schematically shows a graph of the pressure profile during a cardiac cycle, and FIG. 4 schematically shows a presentation of the pressure and the ventricular volume during the cardiac cycle in three standard cases with different end-diastolic filling pressure.

FIG. 1 schematically shows the body 1 of a patient and the heart 2 to be assisted and a rotary pump 3 arranged on the heart. The pump 3 is connected by means of an inlet cannula 4 to the patient's heart 2 and draws in blood from the right ventricle so as to convey this blood to the pump outlet 5 and through the outlet cannula 6 into the aorta 7.

A pressure sensor 8 is provided in the interior of the heart as an element of the control device and is connected by means of a line 9 to a processing device 10 of the control device. The processing device 10 electrically controls the pump 3 under consideration of results of the pressure measurement. To this end, a device 10a firstly associates a value of an operating parameter of the pump, for example a delivery rate of the pump or a pump speed, with an end-diastolic filling pressure. For this purpose, the device 10a is connected to a memory device 10b.

One problem here is the changing blood flow rate requirement in the patient's body. Usually, a more intense circulation of blood is required at many points of the patient's body with increasing physical load, which means that more blood is delivered back to the heart via the venous system (venous return). A physiological control of a heart assistance system must provide measures in order to pump away the blood volume delivered from the right ventricle. In a physiologically functioning heart without assistance, the ejection of the ventricle increases with an increase of the end-diastolic ventricular pressure, so as to be able to pump away the increased delivered blood volume (Frank-Starling effect). A similar control system can be replicated by means of the proposed innovation, i.e. a control system that does not deliberately keep the end-diastolic filling pressure constant, but nevertheless responds to changes in the end-diastolic filling pressure.

To this end, the mechanism of the control system will firstly be described in principle on the basis of FIG. 2. FIG. 2 describes a control circuit in which a target value for the end-diastolic filling pressure is specified at the input 11. A microcontroller, which is arranged in the processing device 10, in a method step 12 for example specifies the speed of the delivery rate as a parameter of the pump depending on the current end-diastolic filling pressure. The controller comprises a memory device, in which the target speed of the pump or a target delivery rate is associated with a certain control variable, such as a current strength or another electric control variable, by means of which the pump is controlled (step 13). A certain pressure is established in the ventricle on this basis (step 14). This is measured continuously by a sensor measurement 15, and in a method step 16 the end-diastolic filling pressure of the periodic cardiac activity is identified from the pressure profile. A signal smoothing operation can then be performed in a filter step 17, and the end-diastolic filling pressure actually achieved is provided jointly with the target pressure at the input 11 of the control loop.

FIG. 2 does not provide any details regarding the nature of the control; for example, it does not have to be the case that the control minimises the difference between the end-diastolic filling pressure actually established and the target value of the end-diastolic filling pressure. However, the deviation of the current end-diastolic filling pressure from the target value can be processed in the controller to provide certain control values of the pump.

The pressure profile in the left ventricle is schematically illustrated in principle on the basis of FIG. 3. The time in seconds is plotted here on the horizontal axis, whereas the pressure in millimetres of mercury is plotted on the vertical axis. The consideration should start at the time t1 shortly after 11.2 seconds, when the pressure in the left ventricle decreases, i.e. the ventricle relaxes. After the active relaxation phase, the filling phase of the ventricle starts, and the ventricle pressure reaches its absolute minimum, which is emphasised by the first marked circle 18. As the ventricle fills, the ventricular pressure slowly rises, until the left ventricle contracts in the systole. At the start of the systole, in the isovolumetric contraction phase, the pressure rises suddenly. At the transition between the slow rise in the diastole and the quick rise in the systole, the end-diastolic filling pressure can be found, marked by the circle 19.

In the event of a change to the physiological load of the patient, both the minimum diastolic pressure 18 and the end-diastolic filling pressure 19 change. Experience has shown that the end-diastolic filling pressure 19 changes to a greater extent, in absolute units, than the minimum diastolic pressure, and therefore a control system that is based on the end-diastolic filling pressure is much less sensitive than a control system that proceeds from the establishment of the minimum diastolic pressure. Sensor drifts and measurement errors are weighted significantly less heavily in this way.

FIG. 4 shows, by way of example and schematically, how the targeted control system acts similarly to a physiologically controlled heart. To this end, the filling volume of the left ventricle is plotted on the horizontal axis, whereas the pressure in the ventricle is plotted on the vertical axis. In a first case, blood flows into the left ventricle starting from point 20 of the graph, so that the volume and pressure change in the direction of the arrow 21 up to the point 28. The point 28 denotes the end-diastolic filling pressure at the given volume. From there, the pressure rises along the line 25 in the direction of the arrow 22, and the volume along the arrow 23 reduces due to ejection of the blood. The pressure then falls back to the starting point 20 along the arrow 24.

If more blood is now delivered from the right ventricle system in the direction of the left ventricle, the volume is increased up to point 29, which also corresponds to a somewhat increased end-diastolic pressure. The pressure is increased accordingly along the line 26, and a greater volume is pumped from the left ventricle along the arrow 23.

The same is true for an even further increased blood volume in the left ventricle when this is filled to the point 30. In this case, the pressure is increased along the line 27 and an even further increased ejection volume (Frank-Starling effect) is pressed out from the ventricle.

The examples shown are intended to show that the physiological control system in no way controls to a constant end-diastolic filling pressure, but instead responds to this filling pressure. There is no correlation between the ejection volume and the end-diastolic filling pressure, and therefore the corresponding control mechanism can be referred to as a P controller. Such a control system can be replicated similarly with the aid of the presented innovation.

An optimal emptying of the left ventricle can be determined using echocardiographic means in order to set the control device optimally. If an optimal delivery rate in the form of a speed of the pump is established for example at 7500 revolutions per minute and if, with this operation, an end-diastolic filling pressure of 12.5 mmHg is given, the control curve can then be set for example in such a way that for each additional millimeter of mercury by which the end-diastolic filling pressure grows, the speed of the pump is increased by 200 revolutions per minute or another specified value. The same should apply accordingly in the case of reduced values of the end-diastolic filling pressure, wherein the relationship between the increase in the end-diastolic filling pressure and the changes to the pump speed can be non-linear. Here, it should be sought to utilise the operating range in respect of the speeds of the pump to the greatest extent possible.

The control can be adjusted at regular intervals by means of an echocardiographic measurement of the delivery volume of the ventricle.

The innovation could thus enable a quasi-physiological control of the delivery capacity of a blood pump, and therefore a patient could achieve greater physical stamina or an increased quality-of-life.

We claim:

1. A control device for a heart pump comprising:
   a processor configured to determine a value for an end-diastolic filling pressure in a ventricle from a pressure profile comprising ventricle pressures sensed during a cardiac cycle, the end-diastolic filling pressure being a pressure in the ventricle at a transition point where diastole ends and systole starts; and
   a memory device comprising a plurality of values for the end-diastolic filling pressure, a plurality of corresponding values characterising an operating parameter of the pump, and an association between the plurality of values for the end-diastolic filling pressure and the plurality of corresponding values characterising the operating parameter of the pump, wherein a non-linear, static relationship exists in the memory device between the values for the end-diastolic filling pressure and the corresponding values characterising the operating parameter of the pump, and wherein the memory device is configured to store a plurality of ranges of the determined end-diastolic filling pressure, wherein each of the ranges is stored in association with a corresponding controller gain;

wherein the processor is configured to determine a value characterising the operating parameter of the pump, based on the determined value for the end-diastolic filling pressure, from the association between the values for the end-diastolic filling pressure and the corresponding values characterising the operating parameter; and wherein the processor is configured to control the heart pump using the determined value characterising the operating parameter.

2. The control device according to claim 1, wherein the control device is configured to be connected to an absolute pressure sensor configured to be arranged in a heart chamber or to another pressure-measuring device.

3. The control device according to claim 2, further comprising a device connected with the absolute pressure sensor that corrects a measured absolute pressure measured from the absolute pressure sensor based on a determined atmospheric pressure.

4. The control device according to claim 1, wherein the control device comprises a proportional controller.

5. The control device according to claim 1, wherein the operating parameter of the pump comprises a pump speed and/or an electric pump capacity.

6. The control device according to claim 1, wherein the operating parameter comprises a delivery rate of a pump, a pump speed, and/or an electric pump capacity.

7. A non-transitory computer readable medium that includes instructions executable by a processor, the computer readable medium comprising:

instructions to determine a value for an end-diastolic filling pressure in a ventricle from a pressure profile comprising ventricle pressures sensed during a cardiac cycle, the end-diastolic filling pressure being a pressure in the ventricle at a transition point where diastole ends and systole starts;

instructions to determine a value characterising an operating parameter of a pump, based on the determined value for the end-diastolic filling pressure, from an association between a plurality of values for the end-diastolic filling pressure and a plurality of corresponding values characterising the operating parameter of the pump, wherein a non-linear, static relationship exists between the values for the end-diastolic filling pressure and the corresponding values characterizing the operating parameter of the pump, and wherein the instructions to determine the value characterising the operating parameter include instructions for determining a controller gain by way of a memory device configured to store a plurality of ranges of the determined end-diastolic filling pressure, wherein each of the ranges is stored in association with a corresponding controller gain; and instructions to control the end-diastolic filling pressure by control of the pump using the determined value characterising the operating parameter of the pump.

8. A method for controlling a heart pump, the method comprising:

determining an association between a plurality of values for an end-diastolic filling pressure and a plurality of corresponding values characterising an operating parameter of the pump using an echocardiographic measurement of an emptying of a left ventricle or of a delivery volume of the left ventricle;

determining a value for the end-diastolic filling pressure in a heart chamber of a heart from a pressure profile comprising heart chamber pressures measured with an absolute pressure sensor during a cardiac cycle, the end-diastolic filling pressure being a pressure in a ventricle at a transition point where diastole ends and systole starts;

determining a value characterising an operating parameter of the pump based on the determined value for the end-diastolic filling pressure from the association between the plurality of values for the end-diastolic filling pressure and the plurality of corresponding values characterising the operating parameter of the pump, wherein a non-linear, static relationship exists between the values for the end-diastolic filling pressure and the corresponding values characterising the operating parameter of the pump, and wherein determining the value characterising the operating parameter comprises determining a controller gain by way of a memory device configured to store a plurality of ranges of the determined end-diastolic filling pressure, wherein each of the ranges is stored in association with a corresponding controller gain; and controlling the end-diastolic filling pressure by controlling the pump using the determined value characterising the operating parameter of the pump.

9. The method according to claim 8, wherein the operating parameter comprises a delivery rate of a pump, a pump speed, and/or an electric pump capacity.

10. The method according to claim 8, wherein controlling the pump comprises controlling the pump with a proportional control and wherein the operating parameter of the pump comprises a pump speed and/or a pump capacity.

* * * * *